United States Patent [19]

McCaulay

[11] 3,956,418

[45] May 11, 1976

[54] ISOPARRAFIN ALKYLATION UTILIZING A CATALYST OF SULFURIC ACID AND HYDROFLUORIC ACID

[75] Inventor: David A. McCaulay, Homewood, Ill.

[73] Assignee: Amoco Oil Company, Chicago, Ill.

[22] Filed: Nov. 27, 1974

[21] Appl. No.: 527,713

[52] U.S. Cl. .......................................... 260/683.63
[51] Int. Cl.² .......................................... C07C 3/54
[58] Field of Search ................. 260/683.63, 683.51, 260/683.59

[56] References Cited
UNITED STATES PATENTS

| | | | |
|---|---|---|---|
| 2,214,481 | 9/1940 | Schmerling et al. | 260/683.63 |
| 2,359,119 | 9/1944 | Karr et al. | 260/683.59 |
| 2,437,544 | 3/1948 | Marisic | 260/683.63 |

Primary Examiner—Delbert E. Gantz
Assistant Examiner—G. J. Crasanakis
Attorney, Agent, or Firm—James R. Henes; Arthur G. Gilkes; William T. McClain

[57] ABSTRACT

An improved process for alkylating at least one alkylatable isoparaffin with at least one alkylating agent selected from the class consisting of an olefin and an alkyl sulfate ester in the presence of a catalyst comprising a major amount of sulfuric acid and a minor amount of hydrofluoric acid.

The invention of this application is related to the inventions of the following applications filed simultaneously with this application and by the same applicant: Ser. No. 527,713 and Ser. No. 527,715.

12 Claims, 2 Drawing Figures

ISOPARRAFIN ALKYLATION UTILIZING A CATALYST OF SULFURIC ACID AND HYDROFLUORIC ACID

BACKGROUND OF THE INVENTION

1. Field of the Invention

This invention relates to method for alkylating an alkylatable isoparaffin with an alkylating agent in the presence of an acid alkylation catalyst. More particularly, this invention relates to a method for alkylating an alkylatable isoparaffin with an alkylating agent selected from the class consisting of an olefin and an alkyl sulfate ester in the presence of a mixture of hydrofluoric acid and sulfuric acid as the alkylation catalyst.

2. Description of the Prior Art

In the petroleum industry, alkylation refers to the catalytic reaction of isoparaffins with light olefins, such as ethylene, propylene, butylenes, and amylenes, to produce highly branched paraffins, the alkylate. These branched paraffins are of high octane quality and have relatively low volatility. They are therefore desirable blending components for gasoline.

The concern over air pollution from automobile exhausts has stimulated interest in alkylation. Specifically, legislation in the United States has restricted the use of some ingredients in motor fuels. Limitations are being placed on gasoline additives, such as lead-containing compounds, and limits on the aromatics content have been proposed. Alkylate is not only a highly satisfactory blend stock for present-day gasolines containing lead, but is also desirable in low-lead or no-lead blends. Thus, alkylation may become even more important to the refining industry as a means of producing gasoline with satisfactory antiknock and volatility characteristics.

In particular, isobutane-olefin alkylation, catalyzed by sulfuric acid or hydrofluoric acid, is an important and growing refinery process. U.S. alkylation capacity has approximately doubled in the past 10 years and has now reached over 850,000 barrels per day. Despite the importance and extensive use of alkylation, two areas still remain where substantial improvements can be made: octane number is below potential, and catalyst consumption is high.

Octane numbers could be increased if the alkylation reaction could be made more selective. The ideal isobutane-olefin alkylation reaction is one wherein isobutane adds to a butene to give trimethylpentanes, which have, in general, the highest octane numbers. Reaction conditions are set to produce this high octane number product by maintaining high isobutane to olefin concentrations to minimize olefin-olefin reactions. Yet, in spite of this, about 40% of the olefin reactant polymerizes to a $C_{12}$ species, which reacts further to give a mixture of hydrocarbons from $C_5$ to $C_{13}$, having octane numbers ranging from 60–90. Therefore, suppression of the polymerization-related reactions would greatly improve gasoline quality.

The formation of by-products also results in high catalyst consumption. Acid-soluble impurities, such as complex polyolefinic hydrocarbons, and oxidative by-products, such as water and sulfonic acids, are the major undesirable by-products. These products dissolve in and react with the acid catalyst so that the spent catalyst has to be withdrawn and replaced by fresh acid continuously. The costs of replacing catalysts are substantial. Any lengthening of catalyst life would reduce costs considerably.

To this end, numerous alkylation catalyst systems have been investigated. Much research activity has been directed towards the use of additives and promoters in catalyst systems to increase yields, improve quality, and reduce acid consumption. For example, the catalyst systems disclosed in U.S. Pat. Nos. 2,427,293; 2,259,723; 2,387,162; 2,441,102; 2,441,103; 2,545,875; 2,591,367; 2,701,184; 3,187,066; 3,221,071; and 3,766,293 are illustrative of catalyst systems for use in the alkylation of isoparaffins with olefins to produce highly branched isoparaffins. Matuszak, U.S. Pat. No. 2,427,293 (1947) discloses a process for first alkylating excess isobutane with isobutylene in the presence of concentrated hydrofluoric acid, separating the resulting hydrocarbon phase from the hydrofluoric acid phase, and alkylating the remaining unreacted isobutane in the separated hydrocarbon phase with normal butene in the presence of concentrated sulfuric acid. This patent discloses the use of both sulfuric acid and hydrofluoric acid as catalyst in an alkylation process but these two catalysts are taught to be used sequentially in a two-step alkylation, not simultaneously in a one-step alkylation. Further, each step in the process of U.S. Pat. No. 2,427,293 involves a different alkylating agent.

On the other hand, the catalyst systems disclosed in U.S. Pat. Nos. 2,259,723; 2,387,162; 2,441,102; 2,441,103; 2,545,875; 2,591,367; 2,701,184; 3,187,066; 3,221,071; and 3,766,293 are illustrative of one-step processes for alkylating an isoparaffin with an olefin. Meadow, U.S. Pat. Nos. 2,441,102 (1948) and 2,441,103 (1948) states in discussions of the prior art that it is known to effect the alkylation of paraffinic hydrocarbons with olefinic hydrocarbons in the presence of alkylation catalysts consisting of mixtures of sulfuric acid and hydrofluoric acid. Cade, U.S. Pat. No. 2,545,875 (1951) discloses alkylation catalysts comprising concentrated hydrofluoric acid, concentrated sulfuric acid, concentrated phosphoric acid, halosulfonic acids, mixtures of the acids mentioned, and aluminum halide-hydrocarbon complexes. These catalysts are sometimes promoted with such materials as hydrogen halides, free halogens, and boron trifluoride. McAllester, U.S. Pat. No. 2,591,367 (1952) discloses alkylation catalysts comprising concentrated sulfuric acid, anhydrous or aqueous hydrogen fluoride, phosphoric acid, chlorosulfuric acid or fluorosulfuric acid, hydrofluoroboric acid, etc. The patent states that the catalyst system may be such individual catalyst acids, mixtures of such acids, or mixtures of one or more such catalysts with other materials having a beneficial effect on the reaction, for example, boron fluoride, phosphorus pentoxide, oxides of vanadium, zinc or cadmium phosphate, sulfur dioxide and/or trioxide. Rupp, U.S. Pat. No. 2,701,184 (1955) contains disclosure of an alkylation catalyst as being any suitable catalyst material in addition to sulfuric acid, such as mixtures of sulfuric acid and phosphoric acid, hydrofluoric acid and certain complexes of aluminum chloride and boron fluoride. Nathan, U.S. Pat. No. 3,187,066 (1965) discloses alkylation catalysts which include mineral acids, such as sulfuric acid, hydrofluoric acid, phosphoric acid, chlorosulfuric acid, fluorosulfuric acid, etc., which may be used either singly or in mixtures. Stahley U.S. Pat. No. 3,221,071 (1965) discloses alkylation catalysts including at least one Friedel-Crafts or Lewis acid catalyst or such catalysts with promoters and states that such Lewis acids include hydrofluoric acid, sulfuric acid, phosphorus pentoxide-sulfuric acid mixtures, orthophosphoric acid, pyrophosphoric acid, and the like. However, the relevant disclosures of these patents were limited to the brief remarks stated hereinabove.

On the other hand, U.S. Pat. Nos. 2,259,723; 2,387,162; and 3,766,292 contain broader disclosures. Ballard et al., U.S. Pat. No. 2,259,723 (1941) discloses an alkylation catalyst comprising a mixture of sulfuric acid, halo-sulfonic acid, or mixtures thereof, and a hydrogen halide, specifically, a hydrogen halide of the class consisting of hydrogen bromide and hydrogen chloride. Matuszak, U.S. Pat. No. 2,387,162 (1945) discloses an alkylation catalyst comprising concentrated hydrofluoric acid, concentrated sulfuric acid, mixtures of sulfuric and hydrofluoric acids, fluorosulfuric acid, chlorosulfuric acid, concentrated hydrofluoric acid containing small proportions of boron trifluoride, boron trifluoride-water complexes, phosphoric acid containing dissolved boron trifluoride, aluminum chloride-hydrocarbon complexes, and the like. Parker et al., U.S. Pat. No. 3,766,293 (1973) discloses an alkylation catalyst comprising a major amount of a strong acid catalyst comprising fluorosulfuric acid and a minor amount of one or more catalyst promoters comprising inorganic acids like hydrofluoric acid or sulfuric acid.

Thus far, no one has disclosed the specific components and the specific proportions thereof that are used in the catalyst system of this invention to thereby produce the unexpected advantages of inhibiting undesirable side reactions, increasing catalyst lifetime, producing the maximum yield of desirable products, and producing the maximum octane number alkylate.

SUMMARY OF THE INVENTION

The method of this invention is an improvement of a process for conducting a liquid-phase alkylation of at least one alkylatable isoparaffin with at least one alkylating agent selected from the class consisting of an olefin and an alkyl sulfate ester in the presence of a mixture of hydrofluoric acid and sulfuric acid as the alkylation catalyst, under alkylation conditions, and in an alkylation reactor, to thereby produce hydrocarbons boiling in the gasoline range. The improvement comprises producing a maximum amount of high-octane hydrocarbons and a maximum octane product and of increasing the effective life of the catalyst, by reacting a mixture containing at least one said alkylatable isoparaffin and at least one said alkylating agent in the presence of a catalyst comprising a major amount of sulfuric acid and a minor amount of hydrofluoric acid.

The alkylatable isoparaffin used in the method of this invention preferably contains from 4 to 10 carbon atoms and more preferably is isobutane. The alkylating agent used in the method of this invention is preferably an olefin containing from 3 to 10 carbon atoms, more preferably a mono-olefin containing from 3 to 5 carbon atoms, even more preferably a mono-olefin containing 4 carbon atoms, and most preferably a straight-chain mono-olefin containing 4 carbon atoms. In the most preferred embodiment of the method of this invention, the alkylating agent is a straight-chain mono-olefin containing 4 carbon atoms, the alkylatable iosparaffin is isobutane, and trimethylpentanes are produced.

The catalyst used in the method of this invention preferably comprises hydrofluoric acid in an amount in the range of from about 1 to about 10 weight percent of the catalyst and sulfuric acid in an amount of at least 85 weight percent of the catalyst and more preferably comprises hydrofluoric acid in an amount in the range of from about 2 to about 6 weight percent of the catalyst and sulfuric acid in an amount of at least 90 weight percent of the catalyst. Most preferably, the catalyst used in the method of this invention consists essentially of hydrofluoric acid and sulfuric acid.

The method of this invention is conducted under at least sufficient pressure to maintain the alkylatable isoparaffin, the alkylating agent, and the catalyst substantially in the liquid phase under the conditions obtaining. The method of this invention is conducted preferably at a temperature in the range of from about 0° to about 20°C., and more preferably at a temperature in the range of from about 2° to about 10°C.

The volume of alkylating agent per volume of catalyst per hour, that is, the volume hourly space velocity (VHSV), in the method of this invention is preferably in the range of from about 0.05 to about 0.8, and more preferably in the range of from about 0.1 to about 0.3. The molar ratio of isoparaffin-to-alkylating agent in the method of this invention is preferably at least 2:1.

DETAILED DESCRIPTION OF THE INVENTION

Figure 1:
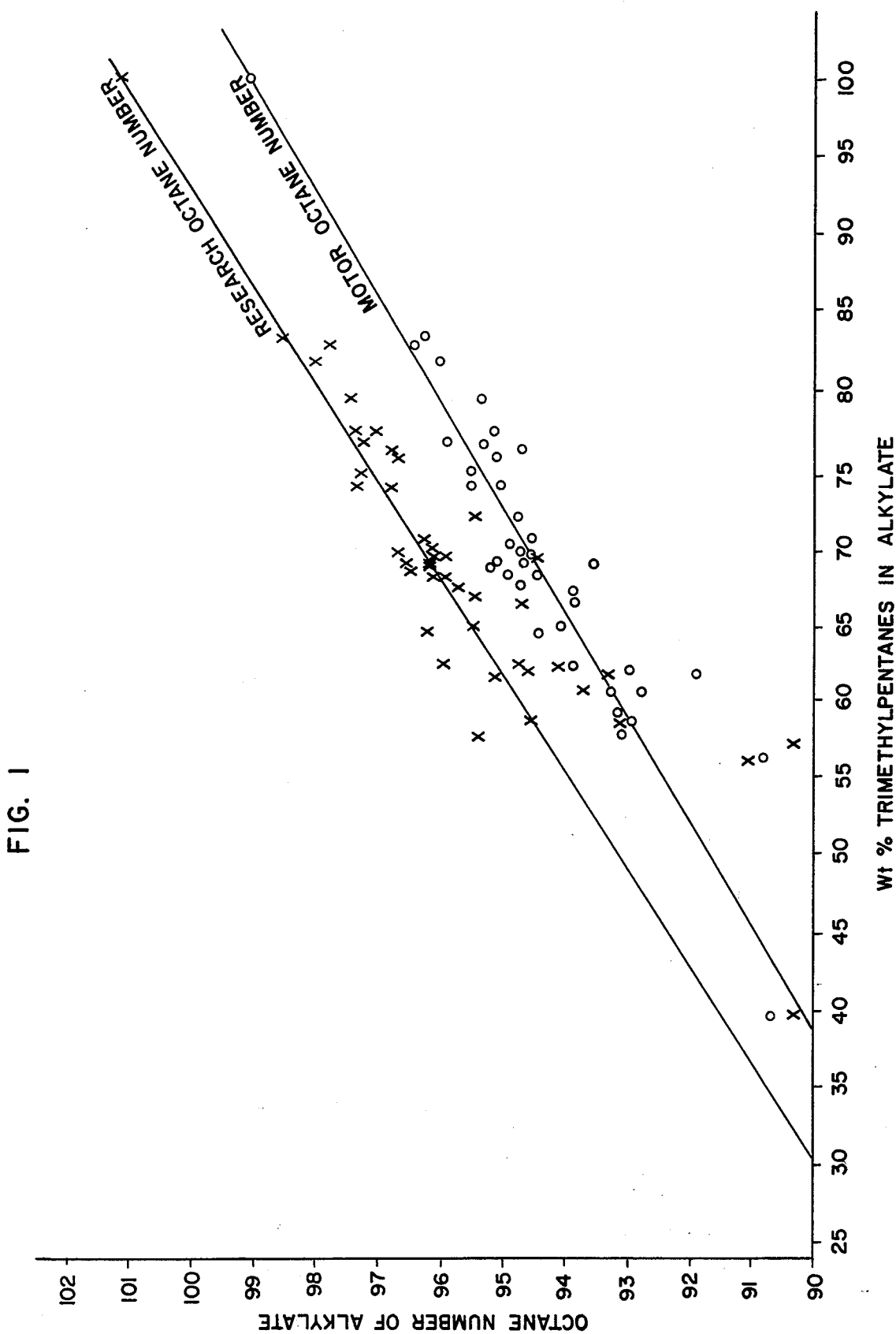
FIG. 1 is a plot of the motor and research octane numbers of a number of alkylates versus the total trimethylpentane content of each of the alkylates.

It has been found that the use of a composite containing a minor amount of hydrofluoric acid and a major amount of sulfuric acid as the catalyst system in an alkylation reaction is advantageous relative to the use of alkylation catalyst systems containing either sulfuric acid alone or mixtures of sulfuric acid, and of larger amounts of hydrofluoric acid than are used in the composite catalyst of this invention.

The catalyst composite of this invention displays improved selectivity in the production of the desired alkylate products, trimethylpentanes, and of a high-octane number alkylate. This increased selectivity results when the catalyst system contains hydrofluoric acid in the range of from about 1 to about 10 weight percent and sulfuric acid in an amount of at least 85 weight percent of the catalyst. Under these conditions, the selectivity of the composite catalyst system of this invention is superior to the selectivities of catalyst systems made up of sulfuric acid alone or mixtures of sulfuric acid and of hydrofluoric acid wherein the concentration of hydrofluoric acid in the composite is less than about 1 weight percent or greater than about 10 weight percent.

The catalyst system of this invention is useful in the alkylation of any suitable alkylatable compound with any suitable alkylating agent in any reactor and flow system conventionally used in alkylation. Suitable alkylatable compounds include isoparaffins and organic compounds containing isoparaffinic groups. Suitable alkylating agents include olefins and alkyl sulfate esters. In particular, the alkylation reaction may be carried out in any suitable form of apparatus and with a variety of isoparaffins and olefins, such as are capable of entering into the low-temperature alkylation reaction in the presence of the catalyst system of this invention.

Olefins are rapidly and nearly irreversibly absorbed in the acid alkylation catalyst and can undergo undesirable polymerization reactions in the acid phase. In order to limit such undesirable side reactions, the concentration of olefins in the acid phase must be kept at a minimum. Reactor design should also minimize high local concentrations of olefins wherever olefins are added to the reactor. Further, a relatively high ratio of isoparaffin-to-olefin in the feed to the reactor is conducive to obtaining the desired reaction products. Since the isoparaffinic products in the alkylate can also be alkylated, a high concentration of isoparaffinic reactant in the reactor effluent has the effect of minimizing undesirable secondary reactions.

Good reactor performance and good alkylate quality require that the acid and hydrocarbon in the reaction zone be sufficiently agitated to form an emulsion, with acid as the continuous phase. Since the alkylation reaction takes place in the acid phase, and, since high degrees of agitation are desired, the acid-continuous emulsion is preferred. The acid-to-hydrocarbon volume ratio in the emulsion should be greater than 1 in order to achieve a hydrocarbon-in-acid emulsion. The exact ratio, being influenced by acid strength, feedstock composition, and mixer characteristics, varies from unit to unit.

Undesirable side reactions occur at high temperatures, and generally use of lower temperatures results in better quality alkylate, that is higher octane number alkylate. The reaction pressure need only be high enough to insure that the hydrocarbons and acid catalyst are liquids at the desired reaction temperature.

EXAMPLES 1-16

Examples 1-16 involve batch alkylations. At the start of each run, a single batch of catalyst and 60 milliliters (33.6 grams) of isobutane were added to a 300-milliliter stainless steel autoclave, equipped with a magnetic stirrer and motor and supplied by Autoclave Engineers, Inc., Erie, Penna. The catalyst systems employed were prepared from acids having known concentrations. The autoclave was closed and was then pressurized to the desired reaction pressure with nitrogen. This mixture was stirred with the magnetic stirrer so that a hydrocarbon-in-acid emulsion would form. While stirring, 15 milliliters of olefin feed was passed into the autoclave at a uniform rate of about 0.25 milliliter per minute, and the alkylation reaction commenced. Since alkylation is highly exothermic, the autoclave was maintained at the desired reaction temperature in a cooling bath containing copper coils through which a solution of ethylene glycol refrigerant flowed.

After all the olefin had been added, stirring in the autoclave was stopped, and the reaction mixture therein was allowed to settle for 15 minutes and separate into and acid phase and a hydrocarbon phase. The supernatant hydrocarbon layer was then withdrawn. The same batch of catalyst was then treated repeatedly in exactly the same way until several batches of hydrocarbon product had been made. Each removed hydrocarbon product was analyzed by gas chromatography and was then fractionated to separate unreacted isobutane from the alkylate. The alkylate was also analyzed by gas chromatography. At the end of the run, a sample of acid was withdrawn from the autoclave for analysis.

The withdrawn sample of acid catalyst was titrated with standard base. The type of titration to determine acid strength at the end of a run differed from run to run, depending upon the particular acid catalyst used. If the acid catalyst was sulfuric acid alone, the acid was simply titrated with standard sodium hydroxide to determine the acid concentration. If the acid catalyst was mixture of hydrofluoric acid and sulfuric acid, the mixture was first titrated with standard sodium hydroxide to determine the total concentration of hydrofluoric and sulfuric acids. The titrated mixture was then titrated a second time with a standard thorium solution in order to determine the concentration of fluoride ion and, hence, the concentration of hydrofluoric acid. The concentration of sulfuric acid alone was then determined by difference.

The amount of acid-soluble impurities formed in the acid catalysts was determined by the difference in the acid catalyst concentration at the start of a run and at the end of the run. The amount of diluent formed per unit time was estimated to be the ratio of this value to the run time. The product of this ratio with any particular on-stream time of the catalyst, therefore, permits a calculation of the concentration of acid-soluble diluent at any chosen time. The total amount of catalyst consumed during a time period was calculated as the amount of catalyst that would have to be removed at the end of the period and replaced by fresh catalyst in order to bring the composition back to what it was at the beginning of the period. The amount of catalyst that was consumed was related to the amount of alkylate produced and was reported as pounds of catalyst per gallon of alkylate.

The experimental conditions employed and the results obtained in the five alkylation runs involved in Examples 1-16 are shown in Tables 1 and 2, respectively. Each alkylation run was performed at 43°F. and under a pressure of approximately 70-90 pounds per square inch guage.

Batches of hydrocarbon products were collected periodically during each alkylation run — generally at each hour after the alkylation run had begun. The alkylate in each batch collected was anaylzed. The alkylate batches collected during a particular time period during the alkylation run were combined. Each such time period corresponded to a particular time of exposure of the catalyst used in that run to reactants and reaction products and constituted one Example. Thus, Examples 1 and 2 involve batches of alkylate collected during two different time periods in the same run. Examples 3 and 4 involve batches of alkylate collected during two different time periods in another single alkylation run. Examples 5-7 involve batches of alkylate collected during three different time periods in a third single run. Examples 8-11 involve batches of alkylate collected during two different time periods in a fourth single run, and Examples 12-16 involve batches of alkylate collected during five different time periods in a fifth single run. The alkylation run, the reaction time period during that run, and the number of the batches collected during that time period are shown in Table 1 for each Example. The average alkylate composition of the combined batches involved in each Example was then estimated. Octane numbers were then calculated from the average and maximum trimethylpentane content of these combined alkylate batches. Calculation of the octane numbers for the combined batches which were collected during one reaction time period in a run involving one catalyst system and the octane numbers for the combined batches which were collected during the corresponding reaction time period in a different run involving a different catalyst system permitted comparison of the performance of the different catalyst systems during comparable reaction time periods and, hence, at comparable periods of exposure of the catalyst to the reactants and reaction products.

$$Y_1 = 0.164 X + 84.9$$

$$Y_2 = 0.15 X + 84.2$$

where X is the total concentration of trimethylpentanes in the alkylate, and $Y_1$ and $Y_2$ are the research and motor octane numbers, respectively. These correlations permit estimates to be made of octane numbers for an alkylate from its trimethylpentane content. They also permit comparisons to be made between the octane ratings of several different alkylates from the tri-

TABLE 1

| Example | Catalyst Composition[1] Sulfuric Acid[2] | Hydrofluoric Acid | Catalyst Sample Size[3] | Initial Concentration[1] of Acid-Soluble Oil in Catalyst | Olefin Feed | Alkylation Run Number | Reacting Time Period From | To | Batch Number From | To |
|---|---|---|---|---|---|---|---|---|---|---|
| 1 | 100 | 0 | 126.5 | 0 | Butene-2 | 1 | 0 | 3 | 1 | 3 |
| 2 | 100 | 0 | 126.5 | 0.7 | Butene-2 | 1 | 3 | 5 | 4 | 5 |
| 3 | 88.6 | 11.4 | 142.7 | 0 | Butene-2 | 2 | 0 | 18 | 1 | 18 |
| 4 | 88.6 | 11.4 | 142.7 | 0.8 | Butene-2 | 2 | 18 | 34 | 19 | 34 |
| 5 | 95.6 | 4.4 | 121.9 | 0 | Butene-2 | 3 | 0 | 20 | 1 | 20 |
| 6 | 95.6 | 4.4 | 121.9 | 2.3 | Butene-2 | 3 | 20 | 40 | 21 | 40 |
| 7 | 95.6 | 4.4 | 121.9 | 4.5 | Butene-2 | 3 | 40 | 60 | 41 | 60 |
| 8 | 100 | 0 | 123.7 | 0.0 | A[6] | 4 | 0 | 30 | 1 | 30 |
| 9 | 100 | 0 | 123.7 | 8.3 | A | 4 | 30 | 35 | 31 | 35 |
| 10 | 100 | 0 | 123.7 | 9.7 | A | 4 | 35 | 40 | 36 | 40 |
| 11 | 100 | 0 | 123.7 | 11.0 | A | 4 | 40 | 46 | 41 | 46 |
| 12 | 95.2 | 4.8 | 125.1 | 0.0 | A | 5 | 0 | 30 | 1 | 30 |
| 13 | 95.2 | 4.8 | 125.1 | 6.3 | A | 5 | 30 | 35 | 31 | 35 |
| 14 | 95.2 | 4.8 | 125.1 | 7.4 | A | 5 | 35 | 40 | 36 | 40 |
| 15 | 95.2 | 4.8 | 125.1 | 8.5 | A | 5 | 45 | 50 | 41 | 45 |
| 16 | 95.2 | 4.8 | 125.1 | 9.5 | A | 5 | 55 | 60 | 46 | 51 |

[1]Weight percent.
[2]The sulfuric acid component is made up to 99.5 weight percent of sulfuric acid and 0.5 weight percent of water.
[3]Grams.
[4]The numbers denote the numbers of the hours after the alkylation run began.
[5]The number denotes the specific batches of hydrocarbon product which were produced and collected in a run.
[6]A denotes 40 weight percent isobutylene; 40 weight percent butene-2; 20 weight percent butene-1.

TABLE 2

| Example | Concentration[1] of Trimethylpentanes in Alkylate Average[2] | Maximum | Octane Number Calculated from Trimethylpentane Concentration Average Concentration Research | Motor | Maximum Concentration Research | Motor | Final Concentration[1] of Acid-Soluble Oil in Catalyst | Catalyst Consumption[3] |
|---|---|---|---|---|---|---|---|---|
| 1 | 64.2 | 69.7 | 95.5 | 93.8 | 96.4 | 94.6 | 0.7 | — |
| 2 | 73.7 | 74.7 | 97.0 | 95.2 | 97.1 | 95.3 | 1.0 | 0.9 |
| 3 | 73.5 | 75.0 | 97.0 | 95.2 | 97.2 | 95.4 | 0.8 | — |
| 4 | 70.6 | 72.0 | 96.5 | 94.5 | 96.7 | 95.0 | 1.5 | 0.8 |
| 5 | 81.4 | 81.7 | 98.4 | 96.4 | 98.3 | 96.4 | 2.3 | — |
| 6 | 80.8 | 81.7 | 98.1 | 96.3 | 98.3 | 96.4 | 4.5 | — |
| 7 | 78.8 | 79.8 | 97.8 | 96.0 | 97.8 | 96.0 | 6.8 | 0.5 |
| 8 | 43.9 | 51.0 | 92.2 | 90.8 | 93.3 | 91.8 | 8.3 | 1.3 |
| 9 | 50.8 | 52.6 | 93.3 | 91.9 | 93.6 | 92.1 | 9.7 | 1.1 |
| 10 | 52.6 | 52.5 | 93.6 | 92.1 | 93.6 | 92.1 | 11.0 | 1.0 |
| 11 | 52.0 | 52.7 | 93.5 | 92.0 | 93.6 | 92.1 | 12.7 | 0.9 |
| 12 | 58.5 | 63.0 | 94.6 | 93.0 | 95.3 | 93.7 | 6.3 | 1.3 |
| 13 | 52.7 | 55.2 | 93.5 | 92.0 | 94.0 | 92.5 | 7.4 | 1.1 |
| 14 | 53.0 | 53.0 | 93.7 | 92.1 | 93.7 | 92.2 | 8.5 | 0.95 |
| 15 | 52.3 | 53.0 | 93.6 | 92.0 | 93.7 | 92.2 | 9.5 | 0.85 |
| 16 | 50.8 | 52.3 | 93.3 | 91.8 | 93.5 | 92.0 | 10.8 | 0.75 |

[1]Weight percent.
[2]The average concentration is determined by dividing the summation of the products of the concentration of a given batch times the volume of that batch for each batch collected by the total volume of all such batches combined.
[3]Pounds of catalyst per gallon of alkylate produced.

The octane numbers were calculated from the average and maximum total concentration of trimethylpentanes in the alkylate as determined gas chromatographically. Empirical relationships between research and motor octane numbers and total trimethylpentane concentration in alkylate were determined from the plots of measured values of research and motor octane numbers versus measured total concentrations of trimethylpentanes in alkylate, as shown in FIG. 1. The best straight lines through the plots in FIG. 1 were determined visually. From these straight lines, the following correlations were found:

methylpentane contents of such alkylates. Extensive experience has shown that qualitative trends in alkylate quality can be predicted equally well by both octane numbers determined from the knock test and octane numbers calculated as indicated hereinabove.

Comparison of the results shown in Table 2 for a particular olefin feed and for a particular reaction time period indicates that the alkylate produced using a catalyst system containing about 4 weight percent of hydrofluoric acid generally had a higher octane rating than the alkylates produced using catalyst systems containing either about 11 weight percent of hydrofluoric acid or no hydrofluoric acid. Further, for a particular reaction time period, the catalyst consumption in the alkylation using the catalyst system containing about 4 weight percent of hydrofluoric acid was less then in the alkylation using the catalyst system containing about 11 weight percent of hydrofluoric acid and was generally less than in the alkylation using the catalyst system containing no hydrofluoric acid.

EXAMPLES 17–20

Figure 2:
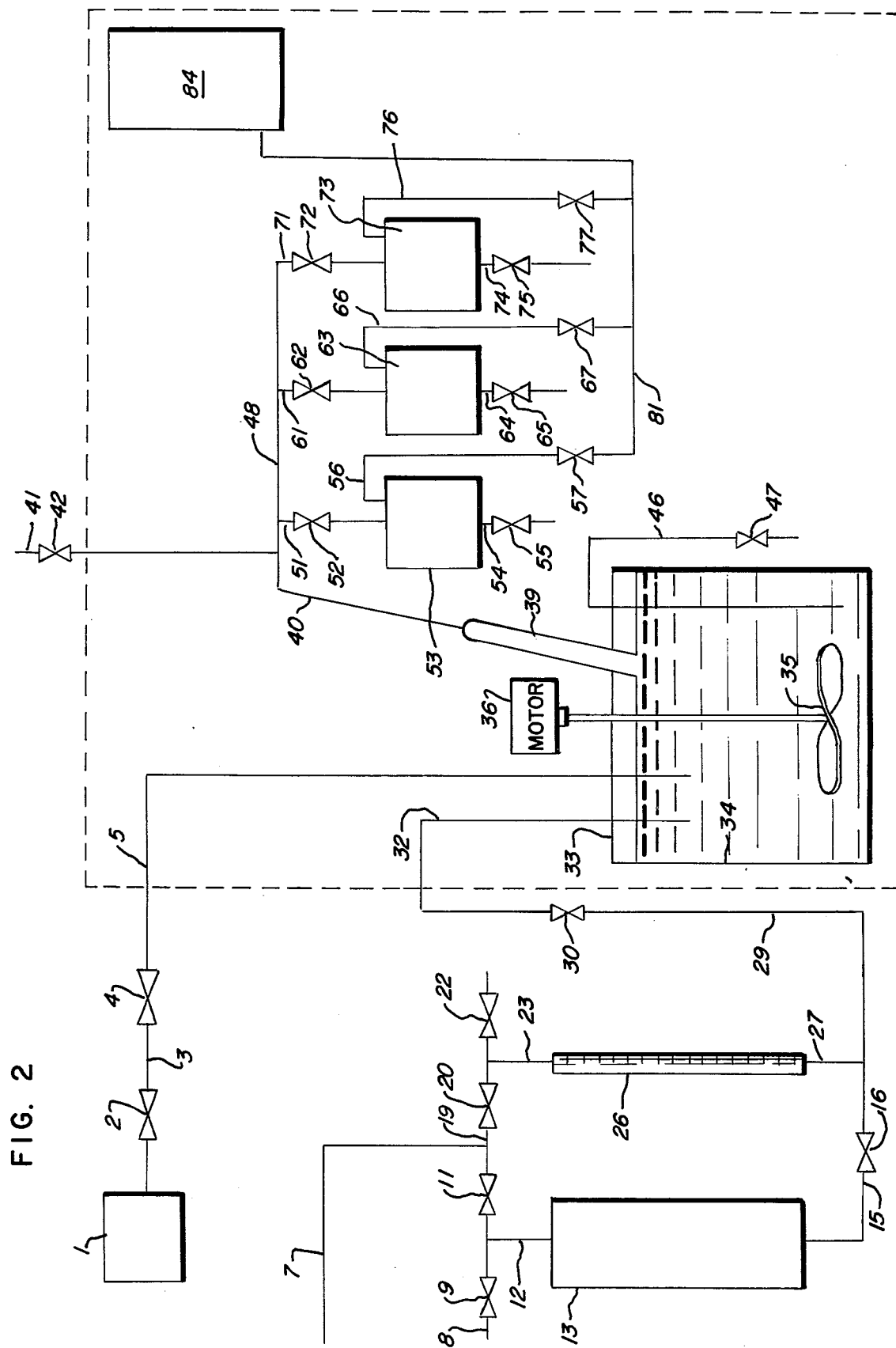
FIG. 2 is a schematic diagram of the system and apparatus used for alkylations performed using the method of this invention, with continuous flow of the hydrocarbon feed.

Examples 17–20 involve alkylations employing continuous flow of the hydrocarbon feed. The mixtures of olefins were supplied by Matheson Gas Products Company. The catalysts were prepared from materials having known concentrations. These alkylations were performed using the apparatus and system shown diagrammatically in FIG. 2.

At the start of each run, with needle valves 42, 52, 62, 72, 57, 67, and 77 open and needle valves 4, 30, 47, 55, 65, and 75 closed, the closed system shown within the dotted lines in FIG. 1 was pressurized up to the desired reaction pressure with nitrogen entering the system through line 41. Then, with needle valves 9, 16, 20, 22, and 30 closed and with needle valve 11 open, nitrogen passed through lines 7, 8, and 12 and into reservoir 13 in order to raise the pressure on the acid catalyst stored in reservoir 13 up to a level higher than the reaction pressure. The needle valve 11 was closed, and needle valve 22 was opened in order to attain atmospheric pressure in graduated Kel-F tube 26 and lines 23, 27, and 29. Next valve 16 was opened, and acid catalyst was allowed to flow from reservoir 13, through lines 15 and 27, and into tube 26 until tube 26 contained the desired volume of catalyst. The level of catalyst in tube 26 was measured. Then, valves 16 and 22 were closed, and valves 21 and 30 were opened so that nitrogen flowed from line 7, through lines 19 and 23, and into tube 26 and forced the desired volume of catalyst from tube 26, through lines 27, 29, and 32 and into 70-milliliter stainless steel autoclave 34, through its top 33. Autoclave 34 was equipped with magnetic stirrer 35 and stirring motor 36 and was supplied by Autoclave Engineers, Inc., Erie, Penna. Autoclave 34 was filled to about one-half its volume with a single batch of acid catalyst. When the desired amount of catalyst had passed into autoclave 34, valves 20, 22, and 30 were closed, and the level of catalyst remaining in tube 26 was measured. The volume of catalyst delivered was determined from the difference in levels of the catalyst in tube 26 before and after delivery of catalyst from tube 26 to autoclave 34.

With needle valve 4 at the intersection of lines 3 and 5 closed, pump 1 was pre-set manually so that the pressure in line 3 was slightly higher than the pressure in line 5. Then, pumping of the hydrocarbon reactants into autoclave 34 commenced. A mixture of isobutane and the butylenes was continuously pumped at a rate of about 30 milliliters per hour by Ruska 500-milliliter syringe-type pump 1, from a container (not shown), through stainless steel lines 3 and 5 and into autoclave 34 through its top 35. Check valve 2 in line 3 prevented backflow of material in line 3, and needle valve 4 served as an on-off control. The flow rate of the hydrocarbon mixture in line 5 was regulated by a setting on the Ruska pump that controlled the movement of the piston.

The acid catalyst and hydrocarbons were mixed by stirrer 35 so that a hydrocarbon-in-acid emulsion would form and so that the alkylation reaction would occur. Since alkylation is highly exothermic, autoclave 34 was maintained at the desired reaction temperature in a cooling bath (not shown) containing copper coils through which a solution of diethylene glycol refrigerant flowed. This emulsion passed into settler 39, which was a transparent Kel-F tube supplied by Auburn Plastic Engineering, Chicago, Ill.

The hydrocarbon product separated from the emulsion in settler 39 and passed overhead through stainless steel line 40 and into stainless steel line 51 containing needle valve 52 and into stainless steel receiver 53. The acid separated and continuously dropped back from tube 39 and autoclave 34. Needle valves 55, 62, and 72 in stainless steel lines 54, 61, and 71, respectively, were closed. During this time, needle valve 57 in stainless steel line 56 was open and needle valves 67 and 77 in stainless steel lines 66 and 76, respectively, were closed to that the empty space in vessel 84 acted as a ballast to keep the pressure nearly constant as receiver 53 gradually filled with liquid product.

After the alkylation had proceeded for a first period of time, needle valves 52 and 57 were closed, and needle valves 62 and 67 were opened, so that the hydrocarbon product in line 48 then psssed into stainless steel receiver 63. After the alkylation had proceeded for a second period of time, needle valve 62 and 67 were closed, and needle valve 72 and 77 were opened, so that the hydrocarbon product in line 48 then passed into stainless steel receiver 73. Stainless steel receivers 53, 63, and 73 were supplied by Hoke Incorporated, Creeskill, N.J. When it was desired to collect alkylate produced during still more periods, additional receivers (not shown) in additional stainless steel lines (not shown) containing additional needle valves (not shown) were employed. Pressure ballast vessel 84 was a large, closed vessel which served to prevent a large build-up of pressure during long runs.

Shortly after hydrocarbon products had been collected in a receiver, the hydrocarbon products were removed therefrom by opening needle valves 55, 65, and 75 in lines 54, 64, and 74, respectively, and these hydrocarbon products were analyzed by gas chromatography. Isobutane was removed from these hydrocarbons products by fractionation. The remaining hydrocarbon fraction was the alkylate and was analyzed by gas chromatography. At the end of the run, the alkylates from selective sequential batches were combined, and knock tests were performed on this combined alkylate to determine the octane numbers.

At the end of a run, stirring in autoclave 34 was stopped, and the reaction mixture therein was allowed to settle and separate into an acid phase and a hydrocarbon phase. Then needle valve 47 in stainless steel line 46 was opened so that a sample of acid from autoclave 34 would pass through line 46 for collection and analysis.

The withdrawn sample of acid catalyst was titrated with standard base. The titrations were performed, and the acid concentrations were determined, as in Examples 1–16. The extent of acid consumption was also calculated as in Examples 1–16.

The experimental conditions employed and the results obtained in Examples 17–20 are shown in Tables 3 and 4, respectively. unlike in Examples 1–16, a different alkylation run was involved in each of these Examples. Each alkylation run employed 35 milliliters of catalyst, a mixture of 40 weight percent of isobutylene, 40 weight percent of butene-2, and 20 weight percent of butene-1, as the olefinic alkylating agent, an olefin space velocity of 0.176, and was performed at 46°F. and under a pressure of 70–90 pounds per square inch gauge.

Batches of hydrocarbon products were collected periodically during each alkylation run. The alkylate in each batch collected was analyzed shortly after being collected. The alkylate batches collected during the time period in the vicinity of the time when the trimethylpentane content of the alkylate passed through a maximum value were combined. The octane rating of each of these combined batches was then determined by the knock test (CFR-Research Method and Motor Method). The average alkylate composition of the combined batches was estimated. Octane numbers were then calculated from the maximum trimethylpentane content of the combined alkylate batches using the correlations described above.

Comparison of the results shown in Table 4 indicates that the alkylate produced using a catalyst system containing 4 weight percent of hydrofluoric acid generally had a higher octane rating than the alkylates produced using catalyst systems containing either 22 weight percent of hydrofluoric acid or no hydrofluoric acid. Further, the extent of catalyst consumption in the alkylation using the catalyst system containing 4 weight percent of hydrofluoric acid was less than in the alkylation using the catalyst system containing 22 weight percent of hydrofluoric acid.

The results of Examples 1–20 illustrate the unexpected improvement in alkylate quality and catalyst lifetime achieved by using a catalyst system comprising hydrofluoric acid in the range of from about 1 to about 10 weight percent and sulfuric acid in an amount of at least 85 weight percent of the catalyst.

I claim:

1. In combination with a process for conducting liquid-phase alkylation of at least one alkylatable isoparaffin with at least one alkylating agent selected from the class consisting of an olefin and an alkyl sulfate ester in the presence of a mixture of hydrofluoric acid and sulfuric acid as the alkylation catalyst, under alkylation conditions, and in an alkylation reactor, to thereby produce hydrocarbons boiling in the gasoline range, the improvement comprising reacting a mixture containing at least one said alkylatable isoparaffin and at least one said alkylating agent in the presence of a catalyst comprising sulfuric acid in an amount of at least 94 weight percent of the catalyst and hydrofluoric acid in an amount in the range of from about 2 to about 6 weight percent, at a temperature in the range of from about 0° to about 20°C., and with a volume ratio of alkylating agent-to-catalyst per hour in the range of from about 0.05 to about 0.8, to thereby produce a maximum amount of high-octane hydrocarbons and a maximum-octane alkylate product and increase the effective life of the catalyst.

2. The process of claim 1 wherein said alkylatable isoparaffin contains from 4 to 10 carbon atoms.

3. The process of claim 2 wherein said alkylatable isoparaffin is isobutane.

4. The process of claim 1 wherein said alkylating agent is an olefin containing from 3 to 10 carbon atoms.

5. The process of claim 4 wherein said olefin is a mono-olefin containing from 3 to 5 carbon atoms.

6. The process of claim 5 wherein said mono-olefin contains 4 carbon atoms.

7. The process of claim 6 wherein said mono-olefin is a straight-chain compound.

8. The process of claim 7 wherein the alkylatable isoparaffin is isobutane and trimethylpentanes are produced.

TABLE 3

| Example | Catalyst Composition[1] Sulfuric Acid[2] | Catalyst Composition[1] Hydrofluoric Acid | Initial Concentration[1] of Acid-Soluble Oil in Catalyst | Volume Ratio of Isobutane-to-Olefin | Length[3] of Run | Averaging Period[4] From | Averaging Period[4] To |
|---|---|---|---|---|---|---|---|
| 17 | 100 | 0 | 0 | 4 | 254 | 106 | 200 |
| 18 | 95 | 5 | 0 | 4 | 93 | 0 | 93 |
| 19 | 78 | 22 | 0 | 5 | 119 | 2 | 28 |
| 20 | 78 | 22 | 4.7 | 3 | 74 | 0 | 74 |

[1]Weight percent.
[2]The sulfuric acid component is made up of 98 weight percent of sulfuric acid and 2 weight percent of water.
[3]Hours.
[4]The number denotes the specific hour during the run.

TABLE 4

| Example | Concentration[1] of Trimethylpentanes in Alkylate Average[2] | Concentration[1] of Trimethylpentanes in Alkylate Maximum | Reaction Time[3] for Maximum Trimethylpentane Concentration | Concentration[1] of Acid-Soluble Oil In Catalyst At Maximum Trimethylpentane Concentration | Catalyst Consumption[4] | Octane Numbers From Knock Test Research | Octane Numbers From Knock Test Motor | Octane Numbers Calculated From Maximum Trimethylpentane Concentration Research | Octane Numbers Calculated From Maximum Trimethylpentane Concentration Motor |
|---|---|---|---|---|---|---|---|---|---|
| 17 | 62.4 | 62.4 | 120 | 7 | 0.34 | 96.1 | 93.9 | 95.2 | 93.6 |
| 18 | 64.6 | 66.4 | 93 | 6 | 0.35 | 96.3 | 94.5 | 95.8 | 94.2 |
| 19 | 60.7 | 63.5[6] | 0 | 7.8[6] | 0.40 | 95.2 | 93.3 | 95.4[5] | 93.7[5] |
| 20 | 39.5 | 43.5[6] | 0 | 12.5[6] | 0.40 | 92.1 | 89.7 | 91.5[5] | 90.1[5] |

[1]Weight percent.
[2]The average concentration is determined by dividing the summation of the products of the concentration of a given batch times the volume of that batch for each batch by the total volume of all such batches combined.
[3]Hours.
[4]Pounds of catalyst per gallon of alkylate.
[5]Value at the start of the averaging period.
[6]Value at the finish of the averaging period.

9. The process of claim 1 wherein the reaction is conducted under at least sufficient pressure to maintain said alkylatable isoparaffin, said alkylating agent, and said catalyst substantially in the liquid phase under the conditions obtaining.

10. The process of claim 1 wherein the reaction is conducted at a temperature in the range of from about 2° to about 10°C.

11. The process of claim 1 wherein the volume ratio of alkylating agent-to-catalyst per hour is in the range of from about 0.1 to about 0.3.

12. The process of claim 1 wherein the molar ratio of alkylatable isoparaffin-to-alkylating agent is at least 2:1.

* * * * *